United States Patent
McLawhorn et al.

(10) Patent No.: US 8,979,891 B2
(45) Date of Patent: Mar. 17, 2015

(54) MEDICAL DEVICES WITH DETACHABLE PIVOTABLE JAWS

(75) Inventors: Tyler Evans McLawhorn, Winston-Salem, NC (US); Michelle D. Martinez, Winston-Salem, NC (US); Vihar C. Surti, Winston-Salem, NC (US); John Crowder Sigmon, Jr., Greensboro, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 402 days.

(21) Appl. No.: 13/327,127

(22) Filed: Dec. 15, 2011

(65) Prior Publication Data

US 2012/0165863 A1    Jun. 28, 2012

Related U.S. Application Data

(63) Continuation-in-part of application No. 13/270,784, filed on Oct. 11, 2011.

(60) Provisional application No. 61/423,420, filed on Dec. 15, 2010.

(51) Int. Cl.
*A61B 17/28* (2006.01)
*A61B 17/122* (2006.01)
(Continued)

(52) U.S. Cl.
CPC .............. *A61B 17/122* (2013.01); *A61B 17/08* (2013.01); *A61B 17/10* (2013.01); *A61B 17/1285* (2013.01); *A61B 17/29* (2013.01); *A61B 2017/00473* (2013.01); *A61B 2017/12004* (2013.01);
(Continued)

(58) Field of Classification Search
CPC ........... A61B 2017/2944; A61B 17/08; A61B 17/10; A61B 17/122; A61B 17/128; A61B 17/1285; A61B 2017/00473; A61B 2017/2902; A61B 2017/2931; A61B 2017/2943; A61B 2017/294
USPC .............. 606/139, 142, 143, 205, 1, 206, 207
See application file for complete search history.

(56) References Cited

U.S. PATENT DOCUMENTS

| 720,385 A | 2/1903 | Storle |
|---|---|---|
| 2,614,445 A | 10/1952 | Riordan |

(Continued)

FOREIGN PATENT DOCUMENTS

| DE | 19534320 | 2/1997 |
|---|---|---|
| DE | 19750878 A1 | 5/1999 |

(Continued)

OTHER PUBLICATIONS

OLYMPUS Endo Therapy brochure on the QuickClip2 Long.
(Continued)

*Primary Examiner* — Julian W Woo
*Assistant Examiner* — Shaun L David
(74) *Attorney, Agent, or Firm* — Brinks Gilson & Lione (57) ABSTRACT

Medical systems, devices and methods are provided for engaging tissue, e.g. for clipping tissue, closing a perforation or performing hemostasis. Generally, the medical system including a housing, first and second jaws rotatable relative to the housing, first and second links attached to both the jaws and the housing, and a driver. The housing, first and second jaws, and first and second links form a linkage mechanism that allows the jaws to engage tissue and be left in vivo.

23 Claims, 9 Drawing Sheets

(51) Int. Cl.
*A61B 17/08* (2006.01)
*A61B 17/10* (2006.01)
*A61B 17/29* (2006.01)
A61B 17/128 (2006.01)
A61B 17/00 (2006.01)
A61B 17/12 (2006.01)

(52) U.S. Cl.
CPC . *A61B2017/2931* (2013.01); *A61B 2017/2934* (2013.01); *A61B 2017/2936* (2013.01); *A61B 2017/2939* (2013.01); *A61B 2017/294* (2013.01); *A61B 2017/2944* (2013.01)
USPC .......................................... 606/207; 606/142

(56) References Cited

U.S. PATENT DOCUMENTS

| | | |
|---|---|---|
| 3,958,576 A | 5/1976 | Komiya |
| 4,467,802 A | 8/1984 | Maslanka |
| 4,512,345 A | 4/1985 | Green |
| 4,569,131 A | 2/1986 | Falk et al. |
| 4,733,664 A | 3/1988 | Kirsch et al. |
| 4,763,668 A | 8/1988 | Macek et al. |
| 4,765,335 A | 8/1988 | Schmidt et al. |
| 4,805,618 A | 2/1989 | Ueda et al. |
| 4,950,273 A | 8/1990 | Briggs |
| 5,029,355 A | 7/1991 | Thai |
| 5,100,418 A | 3/1992 | Yoon et al. |
| 5,141,519 A | 8/1992 | Smith et al. |
| 5,152,778 A | 10/1992 | Bales, Jr. et al. |
| 5,174,276 A | 12/1992 | Crockard |
| 5,192,298 A | 3/1993 | Smith et al. |
| 5,201,743 A | 4/1993 | Haber et al. |
| 5,209,747 A | 5/1993 | Knoepfler |
| 5,275,608 A | 1/1994 | Forman et al. |
| 5,275,613 A | 1/1994 | Haber et al. |
| 5,275,615 A | 1/1994 | Rose |
| 5,282,806 A | 2/1994 | Haber et al. |
| 5,318,589 A | 6/1994 | Lichtman |
| 5,368,606 A | 11/1994 | Marlow et al. |
| 5,471,992 A | 12/1995 | Banik et al. |
| 5,571,137 A | 11/1996 | Marlow et al. |
| 5,618,303 A | 4/1997 | Marlow et al. |
| 5,632,764 A | 5/1997 | Beideman et al. |
| 5,702,407 A | 12/1997 | Kaji |
| 5,766,184 A | 6/1998 | Matsuno et al. |
| 5,766,189 A | 6/1998 | Matsuno |
| 5,792,165 A | 8/1998 | Kilieman et al. |
| 5,797,923 A | 8/1998 | Aiyar et al. |
| 5,964,779 A | 10/1999 | Mayenberger et al. |
| 6,059,719 A | 5/2000 | Yamamoto et al. |
| 6,358,197 B1 | 3/2002 | Silverman et al. |
| 6,814,742 B2 | 11/2004 | Kimura et al. |
| 6,923,818 B2 | 8/2005 | Muramatsu et al. |
| 7,011,667 B2 | 3/2006 | Kobayashi et al. |
| 7,041,118 B2 | 5/2006 | Muramatsu et al. |
| 7,081,121 B2 | 7/2006 | Muramatsu et al. |
| 7,223,271 B2 | 5/2007 | Muramatsu et al. |
| 7,223,272 B2 | 5/2007 | Francese et al. |
| 7,326,221 B2 | 2/2008 | Sakamoto |
| 7,452,327 B2 | 11/2008 | Durgin et al. |
| 7,488,334 B2 | 2/2009 | Jugenheimer et al. |
| 7,494,461 B2 | 2/2009 | Wells et al. |
| 7,601,159 B2 | 10/2009 | Ewers et al. |
| 7,722,628 B2 | 5/2010 | Stokes et al. |
| 7,727,247 B2 | 6/2010 | Kimura et al. |
| 7,736,372 B2 | 6/2010 | Reydel et al. |
| 7,736,374 B2 | 6/2010 | Vaughan et al. |
| 7,740,639 B2 | 6/2010 | Hummel et al. |
| 7,744,613 B2 | 6/2010 | Ewers et al. |
| 7,766,810 B2 | 8/2010 | Ohdaira |
| 7,776,057 B2 | 8/2010 | Laufer et al. |
| 7,815,652 B2 | 10/2010 | Messerly et al. |
| 8,083,668 B2 | 12/2011 | Durgin et al. |
| 8,088,061 B2 | 1/2012 | Wells et al. |
| 2002/0151916 A1 | 10/2002 | Muramatsu et al. |
| 2002/0173805 A1 | 11/2002 | Matsuno et al. |
| 2002/0177861 A1 | 11/2002 | Sugiyama et al. |
| 2003/0069592 A1 | 4/2003 | Adams et al. |
| 2003/0097146 A1 | 5/2003 | Montalvo et al. |
| 2004/0044363 A1 | 3/2004 | Fowler |
| 2005/0059985 A1 | 3/2005 | Kimura |
| 2005/0101991 A1 | 5/2005 | Ahlberg et al. |
| 2005/0234296 A1 | 10/2005 | Saadat et al. |
| 2005/0251183 A1 | 11/2005 | Buckman et al. |
| 2005/0272977 A1 | 12/2005 | Saadat et al. |
| 2006/0084886 A1 | 4/2006 | Reydel |
| 2006/0155308 A1 | 7/2006 | Griego |
| 2006/0258905 A1 | 11/2006 | Kaji et al. |
| 2006/0259045 A1 | 11/2006 | Damarati |
| 2007/0073185 A1 | 3/2007 | Nakao |
| 2007/0135678 A1 | 6/2007 | Suzuki |
| 2007/0239162 A1 | 10/2007 | Bhatnagar et al. |
| 2007/0250113 A1 | 10/2007 | Hegeman et al. |
| 2007/0287993 A1 | 12/2007 | Hinman et al. |
| 2008/0004656 A1 | 1/2008 | Livneh |
| 2008/0147113 A1 | 6/2008 | Nobis et al. |
| 2008/0171907 A1 | 7/2008 | Long et al. |
| 2008/0228199 A1 | 9/2008 | Cropper et al. |
| 2008/0228202 A1 | 9/2008 | Cropper et al. |
| 2008/0234703 A1 | 9/2008 | Cropper et al. |
| 2008/0234705 A1 | 9/2008 | Cropper et al. |
| 2008/0255427 A1 | 10/2008 | Satake et al. |
| 2008/0262539 A1 | 10/2008 | Ewers et al. |
| 2008/0269557 A1 | 10/2008 | Marescaux et al. |
| 2008/0269566 A1 | 10/2008 | Measamer |
| 2008/0275441 A1 | 11/2008 | Aue |
| 2008/0287963 A1 | 11/2008 | Rogers et al. |
| 2008/0294178 A1 | 11/2008 | Kortenbach et al. |
| 2008/0300461 A1 | 12/2008 | Shaw et al. |
| 2008/0300624 A1 | 12/2008 | Schwemberger et al. |
| 2009/0005638 A1 | 1/2009 | Zwolinski |
| 2009/0018602 A1 | 1/2009 | Mitelberg et al. |
| 2009/0043316 A1 | 2/2009 | Durgin et al. |
| 2009/0062792 A1 | 3/2009 | Vakharia et al. |
| 2009/0138006 A1 | 5/2009 | Bales et al. |
| 2009/0138028 A1 | 5/2009 | Wells et al. |
| 2009/0143794 A1 | 6/2009 | Conlon et al. |
| 2009/0163934 A1 | 6/2009 | Raschdorf, Jr. et al. |
| 2009/0192344 A1 | 7/2009 | Bakos et al. |
| 2009/0221915 A1 | 9/2009 | Voegele et al. |
| 2009/0299385 A1 | 12/2009 | Stefanchik et al. |
| 2009/0306683 A1 | 12/2009 | Zwolinski et al. |
| 2009/0306686 A1 | 12/2009 | Ohdaira |
| 2009/0326518 A1 | 12/2009 | Rabin |
| 2009/0326578 A1 | 12/2009 | Ewers et al. |
| 2010/0042115 A1 | 2/2010 | Saadar et al. |
| 2010/0057078 A1 | 3/2010 | Arts et al. |
| 2010/0057085 A1 | 3/2010 | Holcomb et al. |
| 2010/0130817 A1 | 5/2010 | Conlon |
| 2010/0168787 A1 | 7/2010 | Surti |
| 2010/0179540 A1 | 7/2010 | Marczyk et al. |
| 2010/0198149 A1 | 8/2010 | Fox |
| 2010/0198248 A1 | 8/2010 | Vakharia |
| 2010/0211086 A1 | 8/2010 | Ewers et al. |
| 2010/0217151 A1 | 8/2010 | Gostout et al. |
| 2010/0217292 A1 | 8/2010 | Kimura et al. |
| 2010/0217293 A1 | 8/2010 | Kimura et al. |
| 2010/0217294 A1 | 8/2010 | Kumura et al. |
| 2010/0249498 A1 | 9/2010 | Wingardner et al. |
| 2010/0249700 A1 | 9/2010 | Spivey |
| 2010/0249808 A1 | 9/2010 | Harada et al. |
| 2012/0016391 A1 | 1/2012 | Aguirre |
| 2012/0109160 A1 | 5/2012 | Martinez et al. |

FOREIGN PATENT DOCUMENTS

| | | |
|---|---|---|
| DE | 19906360 A1 | 8/2000 |
| DE | 102006003548 | 8/2007 |
| JP | 57-156752 | 9/1982 |
| JP | 60-103946 | 6/1985 |
| JP | 63-6016 | 2/1988 |
| JP | 63-267345 | 11/1988 |
| JP | 63-288147 | 11/1988 |

(56) References Cited

FOREIGN PATENT DOCUMENTS

| | | |
|---|---|---|
| JP | 2-6011 | 1/1990 |
| JP | 2007950 | 1/1990 |
| JP | 4-26091 | 3/1992 |
| JP | 4102450 | 4/1992 |
| JP | 5-212043 | 8/1993 |
| JP | 5208020 | 8/1993 |
| JP | 5212042 | 8/1993 |
| JP | 6237939 | 8/1994 |
| JP | 6254101 | 9/1994 |
| JP | 8019548 | 1/1996 |
| JP | 8126648 | 5/1996 |
| JP | 8280701 | 10/1996 |
| JP | 8308847 | 11/1996 |
| JP | 9038093 | 2/1997 |
| JP | 9289989 | 11/1997 |
| JP | 2000-33090 | 2/2000 |
| JP | 2000-335631 | 12/2000 |
| JP | 2001-520069 | 10/2001 |
| JP | 2002-224124 | 8/2002 |
| JP | 2002-301082 | 10/2002 |
| JP | 2002-360585 | 12/2002 |
| WO | WO 9614020 | 5/1996 |
| WO | WO 99/20183 | 4/1999 |
| WO | WO 2004/017839 | 4/2004 |
| WO | WO 2008/005433 | 1/2008 |
| WO | WO 2010/078163 | 7/2010 |
| WO | WO 2011/087723 | 7/2011 |
| WO | WO 2012/051188 | 4/2012 |
| WO | WO 2012/051200 | 4/2012 |
| WO | WO 2015/051200 | 4/2012 |
| WO | WO 2012/083041 | 6/2012 |

OTHER PUBLICATIONS

Cooper Surgical brochure on the Marlow Nu-Tip Laparoscopic Instruments.
Medwork brochure, Endo Therapy for the Clipmaster 3.
Boston Scientific Catalog on the Resolution Clip Device.
Medicon Instrument Catalog, pp. 440, 441, 443, 451, 585, 686 (1986).
V. Mueller, The Surgical Armamentarium, pp. F176-F177 (1988).
Annex to Form PCT/ISA/206—Communication Relating to the Results of Partial International Search for PCT/US2011/055800 (Jun. 28, 2012).
International Search Report/Written Opinion for PCT/US2009/069270 (May 17, 2010).
International Search Report/Written Opinion for PCT/US2010/061077 (Apr. 1, 2011).
International Search Report and Opinion for PCT/US2011/055780 (Jun. 14, 2012).
International Search Report and Opinion for PCT/US2011/055786 (Jun. 19, 2012).
International Search Report and Opinion for PCT/US2011/065200 (Jun. 13, 2012).
International Search Report and Opinion for PCT/US2011/055800 (Sep. 12, 2012).
International Search Report and Opinion for PCT/US2012/046666 (Oct. 8, 2012).
Office Action dated Jan. 18, 2012 for U.S. Appl. No. 12/645,004 in related application.
Office Action dated May 29, 2012 for U.S. Appl. No. 12/645,004 in related application.
Office Action dated Dec. 20, 2012 for U.S. Appl. No. 13/186,427 in related application.

MEDICAL DEVICES WITH DETACHABLE PIVOTABLE JAWS

CROSS-REFERENCE TO RELATED APPLICATIONS

This application is a Continuation-In-Part of U.S. patent application Ser. No. 13/270,784 filed on Oct. 11, 2011, and also claims the benefit of U.S. Provisional Patent Application Ser. No. 61/423,420 filed on Dec. 15, 2010, entitled "MEDICAL DEVICES WITH DETACHABLE PIVOTABLE JAWS," All of the foregoing applications are hereby incorporated by reference.

BACKGROUND

Conventionally, a clip may be introduced into a body cavity through an endoscope to grasp living tissue of a body cavity for hemostasis, marking, and/or ligating. Such clips are often known as surgical clips, endoscopic clips, hemostasis clips and vascular clips. In addition, clips are now being used in a number of applications related to gastrointestinal bleeding such as peptic ulcers, Mallory-Weiss tears, Dieulafoy's lesions, angiomas, post-papillotomy bleeding, and small varices with active bleeding. Clips have also been attempted for use in closing perforations in the stomach Gastrointestinal bleeding is a somewhat common and serious condition that is often fatal if left untreated. This problem has prompted the development of a number of endoscopic therapeutic approaches to achieve hemostasis such as the injection of sclerosing agents and contact thermo-coagulation techniques. Although such approaches are often effective, bleeding continues for many patients and corrective surgery therefore becomes necessary. Because surgery is an invasive technique that is associated with a high morbidity rate and many other undesirable side effects, there exists a need for highly effective, less invasive procedures.

Mechanical hemostatic devices such as clips have been used in various parts of the body, including gastrointestinal applications. One of the problems associated with conventional hemostatic devices and clips, however, is that many devices are not strong enough to cause permanent hemostasis. Further, clips have also been attempted for use in closing perforations in the stomach or gastrointestinal structures, but unfortunately traditional clips suffer from difficult placement and the capability to grasp a limited amount of tissue, potentially resulting in incomplete closure.

SUMMARY

The invention may include any of the following aspects in various combinations and may also include any other aspect described below in the written description or in the attached drawings.

In a first aspect, a medical device is provided for engaging tissue, the medical device including a housing, first and second jaws, first and second links, and a driver. The housing defines an internal passageway and a longitudinal axis extending between proximal and distal ends of the housing. The housing also defines a jaw guide surface, a first link guide surface and a second link guide surface, each of the guide surfaces extending longitudinally between proximal and distal ends of the guide surfaces. The first jaw is slidably and pivotally connected to the housing, and has proximal and distal ends. The first jaw is slidably received within the internal passageway for longitudinal movement along the jaw guide surface. The second jaw is slidably and pivotally connected to the housing, and has proximal and distal ends. The second jaw is slidably received within the internal passageway for longitudinal movement along the jaw guide surface. The first link has first and second ends. The first end is fixedly attached to the first jaw, and the second end is slidably and pivotally attached to the housing for longitudinal movement along the first link guide surface. The second link has first and second ends. The first end is fixedly attached to the second jaw, and the second end is slidably and pivotally attached to the housing for longitudinal movement along the second link guide surface. The driver is operatively connected to the first and second jaws, whereby longitudinal movement of the driver moves the first and second jaws longitudinally along the jaw guide surface and moves the second ends of the first and second links along the first and second link guide surfaces. The distal portions of the first and second link guide surfaces are shaped such that longitudinal movement of the second ends of the first and second links therethrough rotates the first and second jaws relative to the housing.

According to more detailed aspects, the jaw guide surface is arranged parallel to a jaw plane extending through the longitudinal axis, and the first link guide surface extends along a first link path spaced away from the jaw plane, and the second link guide surface extends along a second link path spaced away from the jaw plane. Preferably, the first and second link paths are spaced on opposite sides of the jaw plane, and the first and second links are generally C-shaped and defined by a mid-section interconnecting a proximal-section and a distal-section. The first jaw is substantially positioned on a first side of the jaw plane, and the second jaw is substantially positioned on a second side of the jaw plane, wherein the mid-section of the first link is positioned on the second side of the jaw plane, and the mid-section of the second link is positioned on the first side of the jaw plane. The first and second jaw guide surfaces each have a proximal portion extending parallel to the longitudinal axis, and a distal portion extending transversely relative to the proximal portion. The distal portions of the first and second jaw guide surfaces extend towards the jaw plane.

According to further detailed aspects, a first link pivot pin pivotally connects the second end of the first link to the housing, and a second link pivot pin pivotally connects the second end of the second link to the housing. The driver includes a distal end having at least one slot receiving the first and second link pins, the at least one slot being elongated and slidably receiving the first and second link pins. Preferably, the distal end of the driver includes a first flange laterally spaced apart from a second flange, the at least one slot including a first slot formed in the first flange and receiving the first link pin, and a second slot formed in the second flange and receiving the second link pin. The first link guide surface is defined by a first link slot formed in the housing, and the second link guide surface is defined by a second link slot formed in the housing, wherein the first link slot is positioned on an opposite side of the housing as the second link slot.

According to still further detailed aspects, the distal end of the driver includes driver end surface located distal to the at least one slot, the end surface abutting the proximal ends of the jaws. The driver is engaged with the second ends of the first and second links when the driver is moved distally, and preferably both distally and proximally. The proximal ends of the first and second jaws are slidably and pivotally attached to the housing, and preferably the proximal ends are pivotally attached to the housing about a shared jaw pivot axis. The first ends of the first and second links are non-rotatably attached to the mid-sections of the first and second jaws, respectively. The second ends of the first and second links are slidably and pivotally connected to the housing. Further, the distal portions of the first and second link guide surfaces extend vertically towards each other, and the distal portions of the first and second link guide surface may cross over the jaw guide surface.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION

The terms "proximal" and "distal" as used herein are intended to have a reference point relative to the user. Specifically, throughout the specification, the terms "distal" and "distally" shall denote a position, direction, or orientation that is generally away from the user, and the terms "proximal" and "proximally" shall denote a position, direction, or orientation that is generally towards the user.

Figure 1:
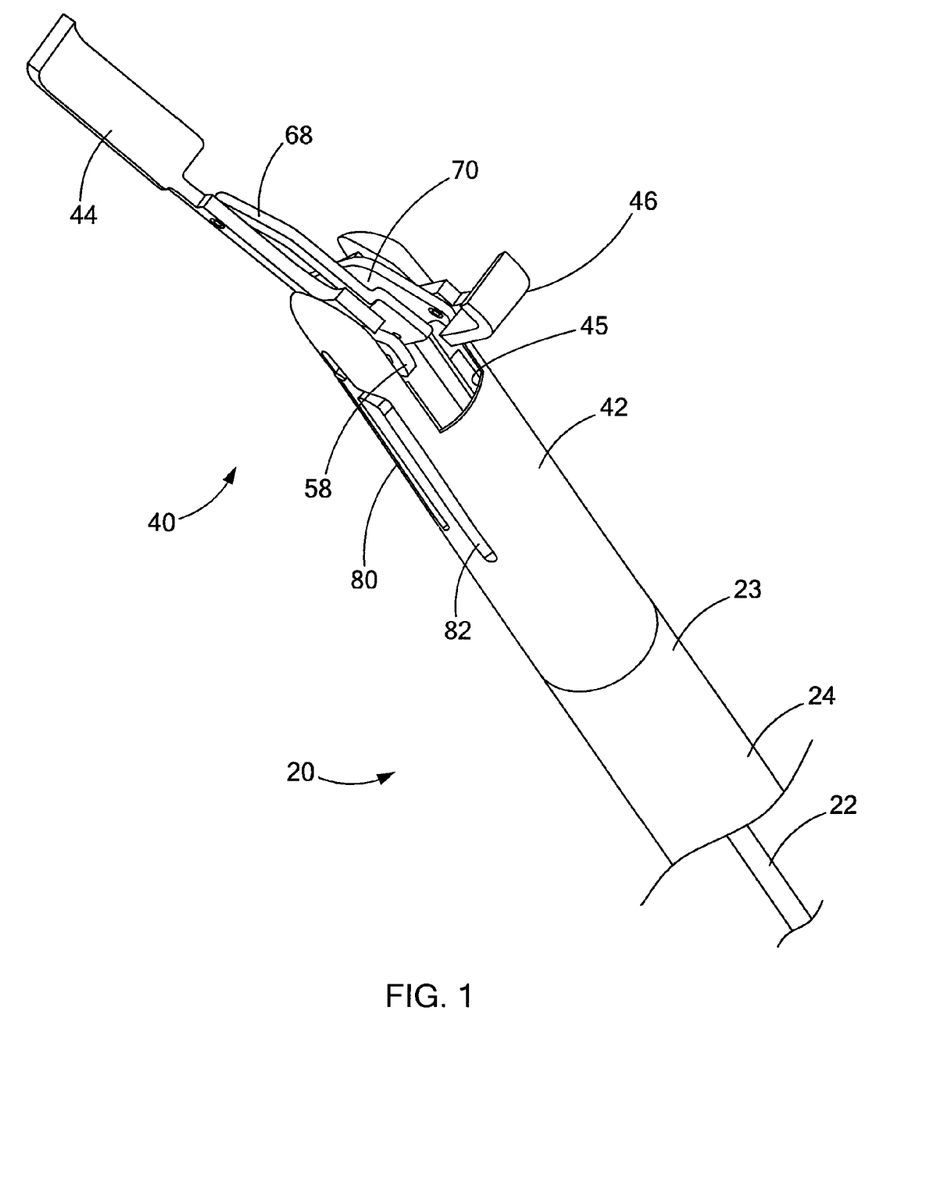
FIG. 1 is a perspective view of a medical system and device constructed in accordance with the teachings of the present invention.
Figure 2:
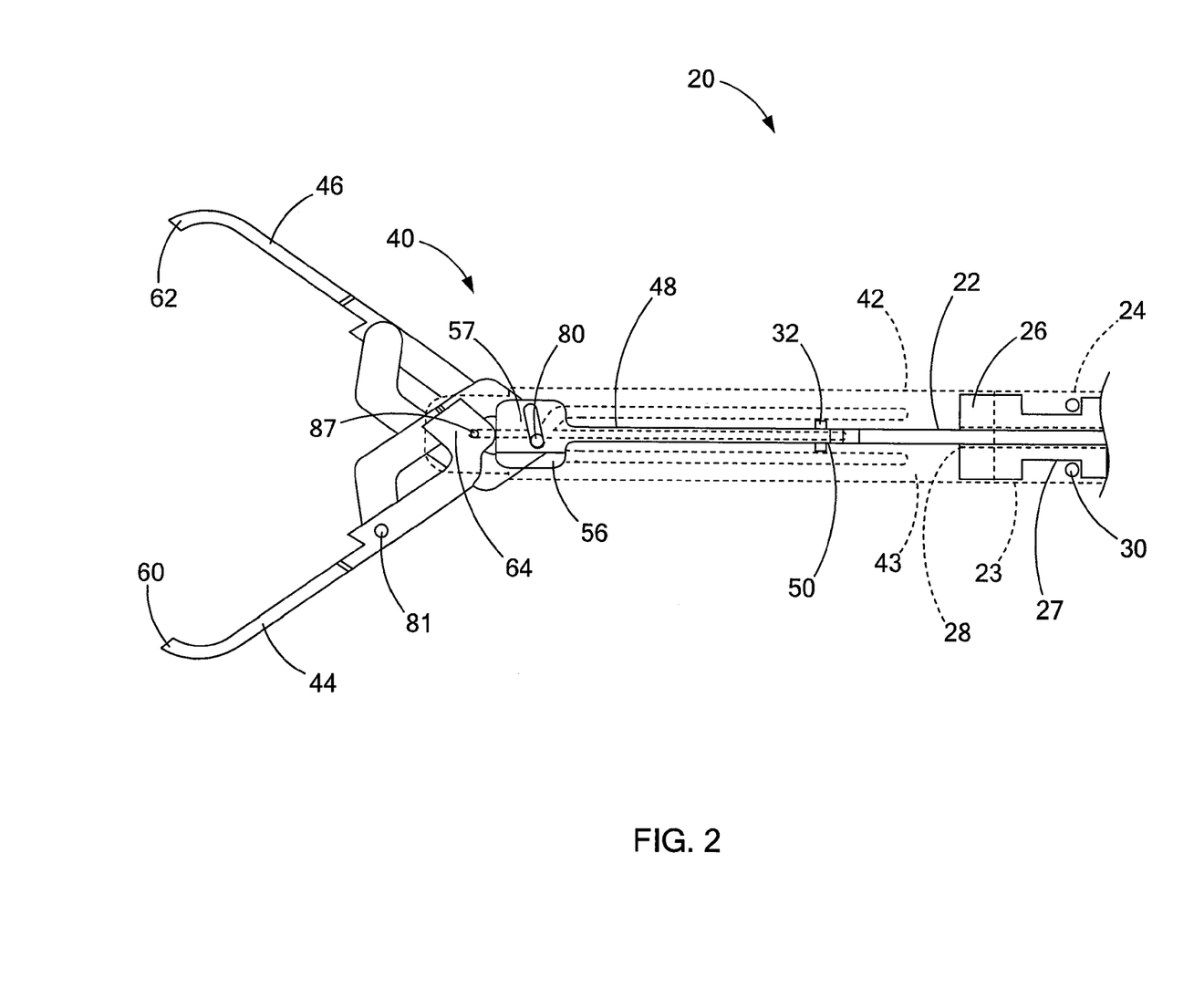
FIG. 2 is a side view of the medical system and device of FIG. 1, having the housing drawn in dashed lines to show the interior components.

An exemplary medical system 20 having a medical device 40 for engaging tissue T (FIG. 9) is shown in FIGS. 1 and 2. The medical system 20 and device 40 are generally sized and structured for operation through the working channel of an endoscope (not shown) or other scope, although the system 20 and device 40 may also be used alone or in conjunction with other elongate devices such as catheters, fiber-optic visualization systems, needles and the like. Generally, the medical system 20 includes a drive wire 22 slidably housed within the distal end 23 of a catheter 24 for selective connection to, and operation of, the medical device 40. As will be described in further detail herein, the medical device 40 generally includes a housing 42 having a first jaw 44 and a second jaw 46 pivotally connected thereto for engaging the tissue T. Generally, the jaws 44, 46 have been shown as forming grasping forceps, although the jaws are intended to be used to clip tissue, e.g. to close an opening or for hemostasis. Accordingly, it will be recognized that the shape and structure of the jaws may take many forms and serve many purposes and functions, all in accordance with the teachings of the present invention.

In the medical system 20, the drive wire 22 slidably extends through the catheter 24. Although the term "wire" is used to refer to the drive wire 22, it will be recognized that any elongate control member capable of transmitting longitudinal force over a distance (such as is required in typical endoscopic, laparoscopic and similar procedures) may be used, and this includes plastic rods or tubes, single filament or multi-filament wires and the like. A connection block 26 is slidably fitted within the distal end 23 of the catheter 24 and defines a bore 28 therethrough which slidably receives the drive wire 22. The exterior of the connection block 26 includes a recessed portion 27, and two pins 30 (e.g., formed from stainless steel wire) are connected to the catheter 24 and positioned within the recessed portion 27 (i.e. between proximal and distal flanges defining the recessed portion 27) to limit the longitudinal movement of the connection block 26.

A distal end of the drive wire 22 defines a distal head 32 that is sized larger than the drive wire 22, and likewise larger than the bore 28 in the connection block 26. As will be described later herein, the distal head 32 is used to slide the connection block 26 within the catheter 24 to disconnect the medical device 40 from the medical system 20. As also seen in FIGS. 1-4, the housing 42 of the medical device 40 is a tubular member defining an interior space 43. A proximal end of the housing 42 frictionally receives a distal end of the connection block 26 within the interior space 43 for selective connection therewith.

The internal passageway 43 of the housing 42 also receives the first and second jaws 44, 46 and a driver 48 which is used to interconnect the drive wire 22 to the jaws 44, 46. As best seen in FIG. 2, the first and second jaws 44, 46 include distal ends 60, 62 that are structured to grasp and engage tissue, which have a talon shape as disclosed in 61/141,934 filed Dec. 31, 2008, the disclosure of which is incorporated herein by reference in its entirety. Generally, distal translation of the driver 48 causes the first and second jaws 44, 46 to rotate outwardly away from each other, while proximal retraction of the driver 48 causes the first and second jaws 44, 46 to rotate inwardly toward one another.

Figure 3:
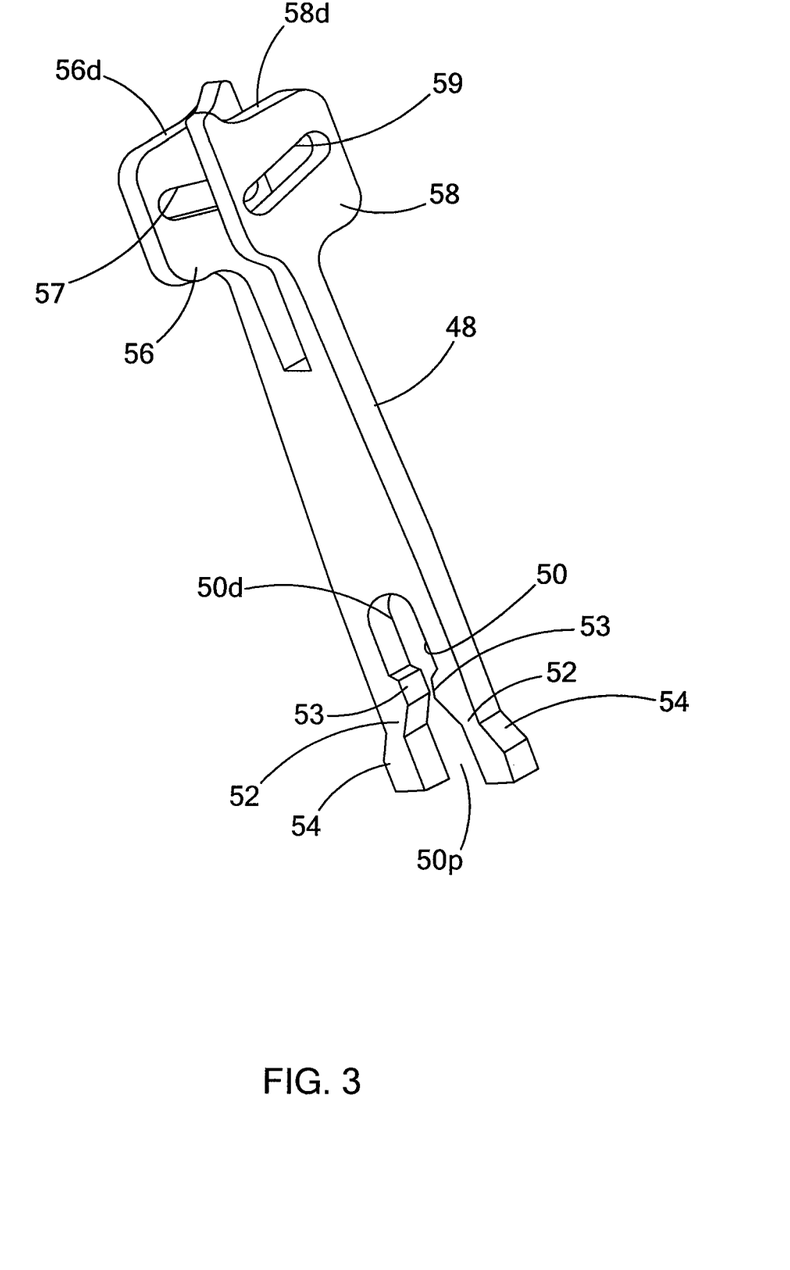
FIG. 3 is a perspective view of a driver forming a portion of the medical system and device of FIG. 1.

As best seen in FIG. 3, the driver 48 has a proximal portion which defines a socket 50 sized to receive the enlarged distal head 32 of the drive wire 22. At the proximal entrance of the socket 50, two deflectable locking tabs 52 are formed which rotate relative to the remainder of the driver 48 to increase or decrease the size of the socket 50. The locking tabs 52 may be separately formed and pivotally attached to the driver 48, or may be integrally formed with the driver 48 and formed of a resilient material which flexes or bends to permit rotation of the locking tabs 52 radially inwardly and radially outwardly. Here, a proximal portion of the locking tabs define slanted shoulders 54 which slope laterally outwardly for engagement with the housing 42 as will be discussed in further detail herein. The locking tabs 52 also include inner projections 53 which project laterally inwardly and separate the socket 50 into a distal portion 50d and a proximal portion 50p.

Figure 4:
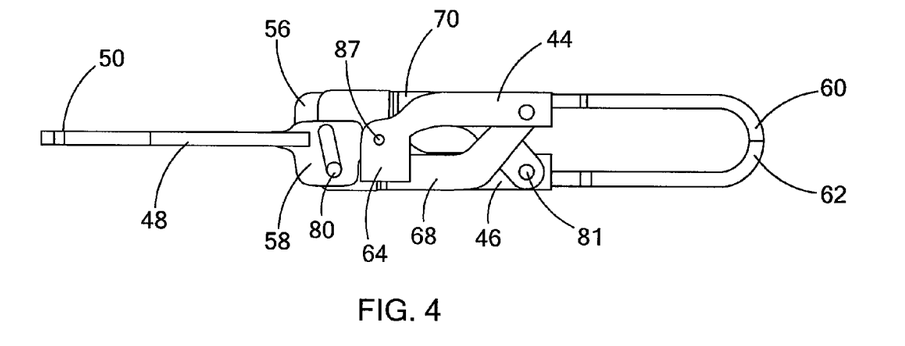
FIG. 4 is a side view of a link forming a portion of the medical system and device of FIG. 1.

As best seen in FIGS. 3 and 4, a distal portion of the driver 48 defines two flanges 56, 58 for engaging and operating the jaws 44, 46. The distal end surface 58d of flange 58 engages a proximal end 64 of jaw 44, while the distal end surface 56d of flange 56 engages a proximal end 66 of jaw 46. The flanges 56, 58 also include elongated slots 57, 59, respectively, for slidable and pivotal connection to two links 68, 70, as will also be further discussed herein. The flanges 56, 58 are shaped to permit and promote rotation of the proximal ends 64, 66 of the jaws 44, 46 relative to the flanges 56, 58 while engaged therewith, and may be flat, curved, or a combination thereof as shown in FIGS. 3 and 4.

Figure 5A:
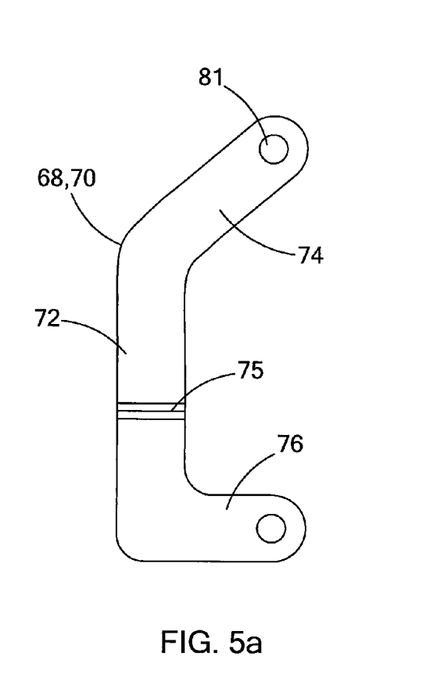
FIG. 5 is a front view of the link shown in FIG. 3.
Figure 5B:
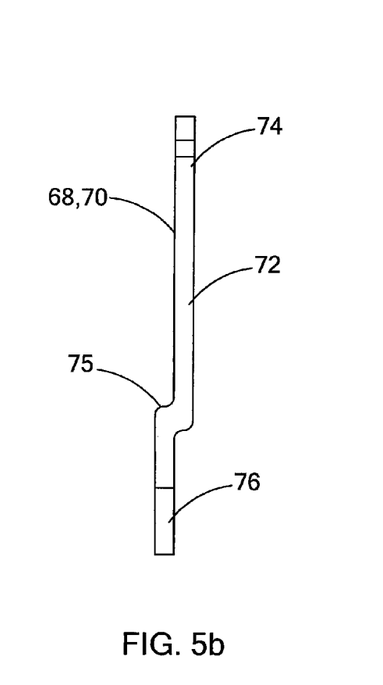

Turning now to FIGS. 5a and 5b, one of the two links 68, 70 is shown from the side and front. Each link 68, 70 is C-shaped member that includes a mid-section 72 interconnecting a distal-section 74 defining a first end, and a proximal-section 76 defining a second end. Both the distal-section 74 and the proximal-section 76 are angled relative to the mid-section 72, the proximal-section 76 being about perpendicular and the distal-section 74 being angled about 45 degrees (preferably within 20-70 degrees) relative to the mid-section. A bend 75 is formed along the mid-section 72 to provide lateral space between the links 68, 70 and the jaws 44, 46 (see, e.g. FIG. 1). As best seen in FIG. 2, the distal-sections 74 of the first and second links 68, 70 are fixedly (non-rotatably) attached to the jaws 44, 46 at points 81, while the proximal-sections are slidably and pivotally attached to the flanges 56, 58 of the driver 48 via pins 80 fitted through the slots 57, 59 therein. The connection points 81 are formed at a midpoint of the first and second jaws 44, 46, i.e. anywhere between the proximal ends 66, 68 and the distal ends 60, 62 of the first and second jaws 44, 46.

Figure 6:
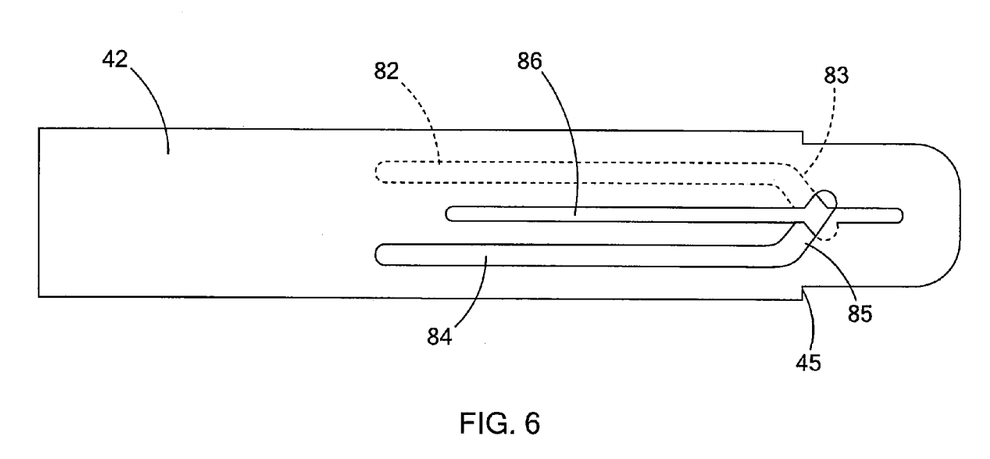
FIG. 6 is a side view of the medical system and device of FIG. 1, having the housing removed to show the interior components.

The housing 42 is shown in FIG. 6. The housing is a tubular member defining three pairs of opposing slots, namely first link slots 82, second link slots 84, and jaw slots 86. The slots are for guiding the first and second links 68, 70 and the jaws 44, 46. Relative to a longitudinal axis of the housing 42, the jaw slots 86 are parallel to the axis and spaced laterally apart (i.e. parallel and co-existing in a lateral jaw plane) while the first and second links slots 82, 84 are spaced vertically apart from the jaw slots 86 (i.e. above and below). The first and second link slots 82, 84 include distal portions 83, 85 that are angled towards each other (vertically inwardly) and extend through the jaw slots 86.

The internal passageway 43 of the housing 42 extends through the distal end of the housing 42, and it is through this passageway 43 that the first and second jaws 44, 46 can extend. Additionally, as shown in FIGS. 1-4, the distal end of the housing 42 defines opposing slots 45 (vertically opposed) which are sized to permit the first and second jaws 44, 46 and the first and second links 68, 70 to pass therethrough when they rotate radially outwardly. Accordingly, it is also clear from FIGS. 1 and 2 that the housing 42 serves to block rotation of the first and second links 68, 70 when they are entirely or partially contained within the internal passageway 43 of the housing 42. Suitable plastics for forming the housing include, but are not limited to, polytetrafluoroethylene (PTFE), expanded polytetrafluoroethylene (EPTFE), polyethylene ether keytone (PEEK), polyvinylchloride (PVC), polycarbonate (PC), polyamide, polyimide, polyurethane, polyethylene (high, medium or low density), and suitable metals include stainless steel, nitinol and similar medical grade metals and alloys.

The proximal ends 64, 66 of jaws 44, 46 are pivotally attached to the housing 42 directly via a shared pin 87 that extends through both proximal ends 64, 66 and through opposing jaw slots 86 formed in the housing. By virtue of the jaw slots 86, the jaws 44, 46 are both pivotally and slidably attached to the housing 42. The opposing jaw slots 86 thus act and define a jaw guide surface of the housing 42 which guides longitudinal movement of the jaws 44, 46 relative to the housing. The distal ends of the jaw slots 86 also serve to restrict the longitudinal movement of the jaws 44, 46 relative to the housing 42. It will be recognized that the jaw guide surface could also be formed by channels, recesses or other structures formed into the housing 42, instead of, or in conjunction with, the jaw slots 86. During assembly, the slots allow the pins of the device 40 to be inserted after the jaws, links and driver are positioned with the housing, and the slots may later be covered with a sleeve, strip, secondary housing or other material if desired.

The proximal ends of the first and second links 68, 70 are slidably and pivotally attached to the housing 42 via the two pins, each denoted by numeral 80. The pins are fitted to the first and second link slots 82, 84 which thus define first and second link guide surfaces of the housing 42 which guide longitudinal movement of the first and second links 68, 70 relative to the housing 42. By virtue of the pins 80 also being connected to the flanges 57, 59 of the driver 48, movement of the drive wire 22 can be transferred to the links, 68, 70 and the jaws 44, 46. As with the jaw guide surface, the first and second link guide surfaces could also be formed by channels, recesses or other structures formed into the housing 42, instead of, or in conjunction with, the first and second link slots 82, 84.

Accordingly, it will be recognized that the jaw guide surface (formed by slots 86) is arranged parallel to the jaw plane extending through the longitudinal axis of the housing 42, and the first link guide surface (formed by slots 82) extends along a first link path spaced away (vertically) from the jaw plane, and the second link guide surface (formed by slots 84) extends along a second link path spaced away (vertically) from the jaw plane. The distal portions 83, 85 of the first and second link slots 82, 84 are angled such that the distal portions of the first and second link paths extend vertically towards the jaw plane, thus guiding the opening/closing of the jaws 44, 46, as will be discussed further herein. It will also be recognized that the first jaw 44 is substantially positioned on a first side of the jaw plane, and the second jaw 46 is substantially positioned on a second side of the jaw plane, while the mid-section 72 of the first link 68 is positioned on the second side of the jaw plane, and the mid-section 72 of the second link 70 is positioned on the first side of the jaw plane.

As shown in FIGS. 1-4, the flanges 56, 58 at the distal end of the driver 48 extend around the proximal-sections 76 of the first and second links 68, 70, and abut the proximal ends 64, 66 of the first and second jaws 44, 46 to first expose and then open the jaws 44, 46, as shown in FIGS. 1 and 2. By sizing the distance between the pins 80, 86 and the distal ends of the slots 82, 84, 86 in the housing 42, relative to the guide surface formed by slots 82, 84, 86, movement of the jaws 44, 46 is effectuated and controlled. Distal translation of the drive wire 22 and driver 48 causes distal translation of the jaws 44, 46 to an extended position outside of the housing 42 where at least a portion of the jaws 44, 46 are exposed. As the jaw pin 87 continues to be moved distally, it passes the point where slots 82, 84 cross over the jaw the slots 86, whereupon the link pins 80 follow the angled distal portions 83, 85 of the first and second link slots 82, 84. Thus, further distal translation of the drive wire 22 and driver 48 causes the pins 80 to move vertically and slide within the slots 57, 59 formed in the driver's flanges 56, 58, and in turn rotate the jaws 44, 46 about their shared jaw pin 87.

Figure 7:
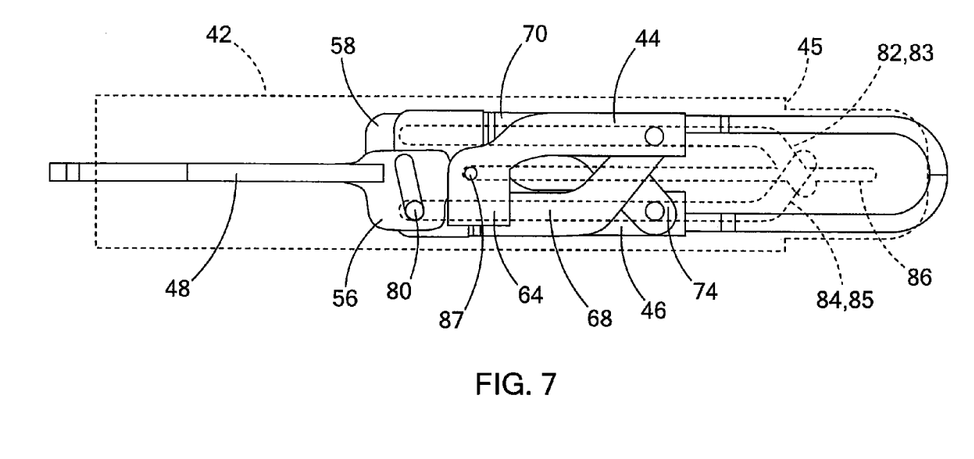
FIG. 7 is a side view of a housing forming a portion of the medical system and device of FIG. 1.
Figure 8:
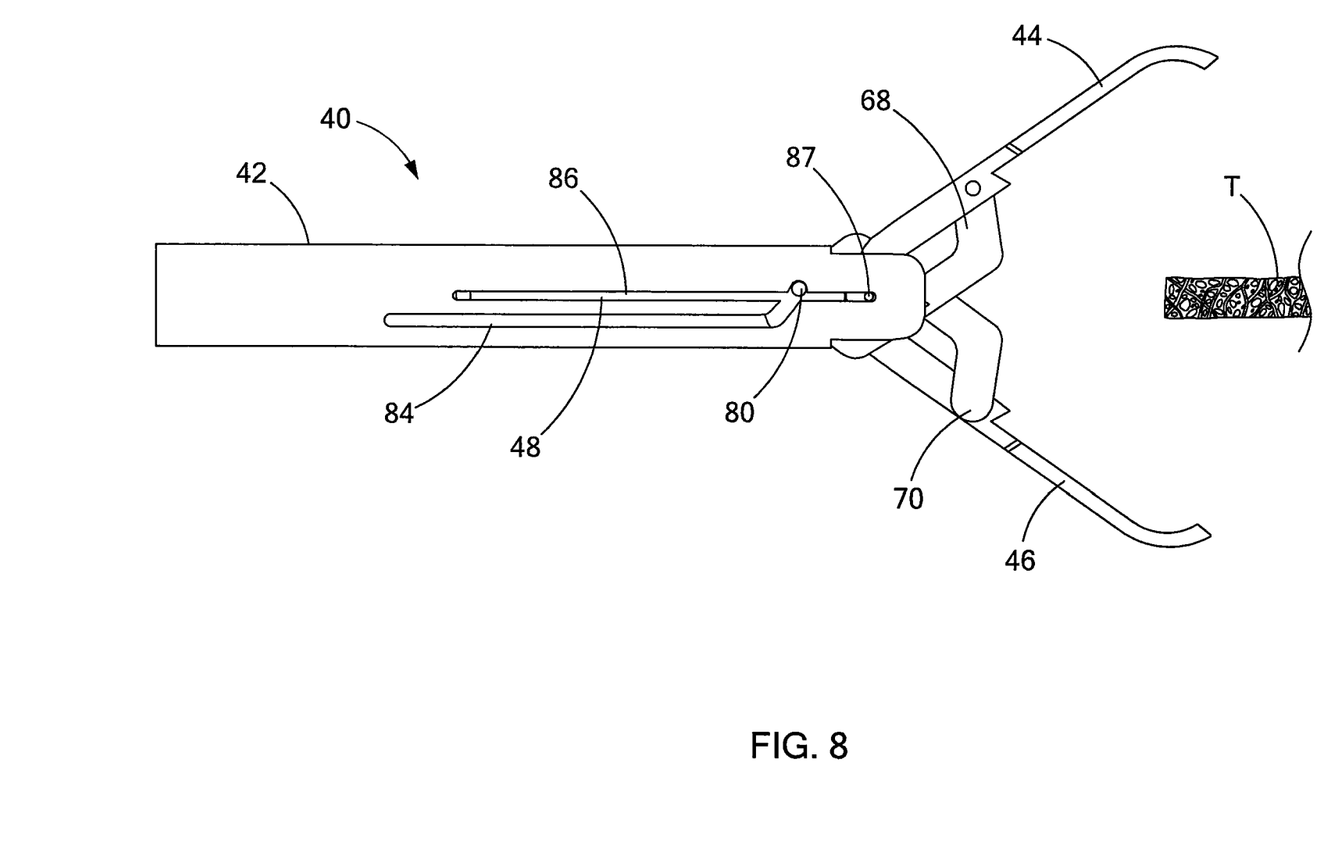
FIGS. 8-10 are side views showing operation of the medical system and device of FIG. 1.

For example, with reference to FIG. 7, since the jaw pin 87 is vertically constrained by slots 86, upward movement of the proximal-section 76 of second link 70 (i.e. along distal portion 85 of slots 84) causes downward movement of the distal-section 74 of the second link 70 since it is fixed to the second jaw 46 which is pivotally connected to the housing 42 via pin 87 and jaw slots 86. Likewise, downward movement of the proximal-section 76 of first link 68 (i.e. along distal portion 83 of slots 82) causes upward movement of the distal-section 74 of the first link 68, and in turn upward rotation of the first jaw 44. In this manner, the jaws 44, 46 rotate outwardly to an open, tissue receiving, position shown in FIGS. 1 and 2.

Eventually, the link pins 80 reach the end of link slots 82, 84, at which point the jaws 44, 46 are fully open. The jaws 44, 46 have been shown rotating about 75°, thus forming a 150° opening between them, however the housing 42 and its slots may be sized to permit rotation through a full 90° or more, thus forming at least a 180° between them. The slots in the housing 42 are sized to permit the rotation of the jaws 44, 46 and links 68, 70 out of the housing, and these slots 45 may also be used to limit the rotation thereof, in addition to or separately from the sizing of the slots 82, 84, 86. It will therefore be seen that the distance and location of the pins 80 (at the ends of the first and second links 68, 70) relative the proximal ends 64, 66 of the jaws 44, 46 and pin 87 determines the rotation of the first and second jaws between a closed configuration and an open configuration.

Figure 9:
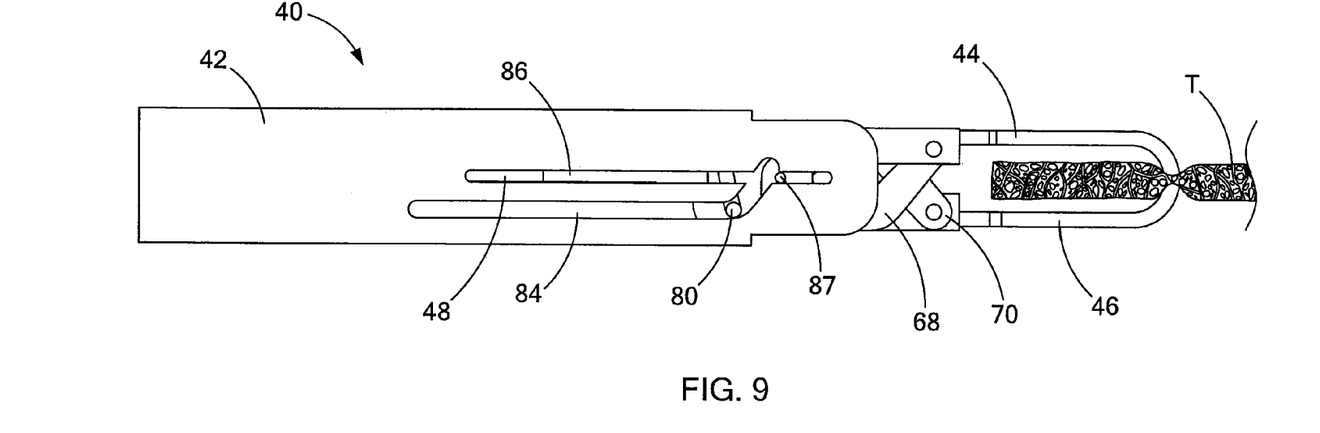
Figure 10:
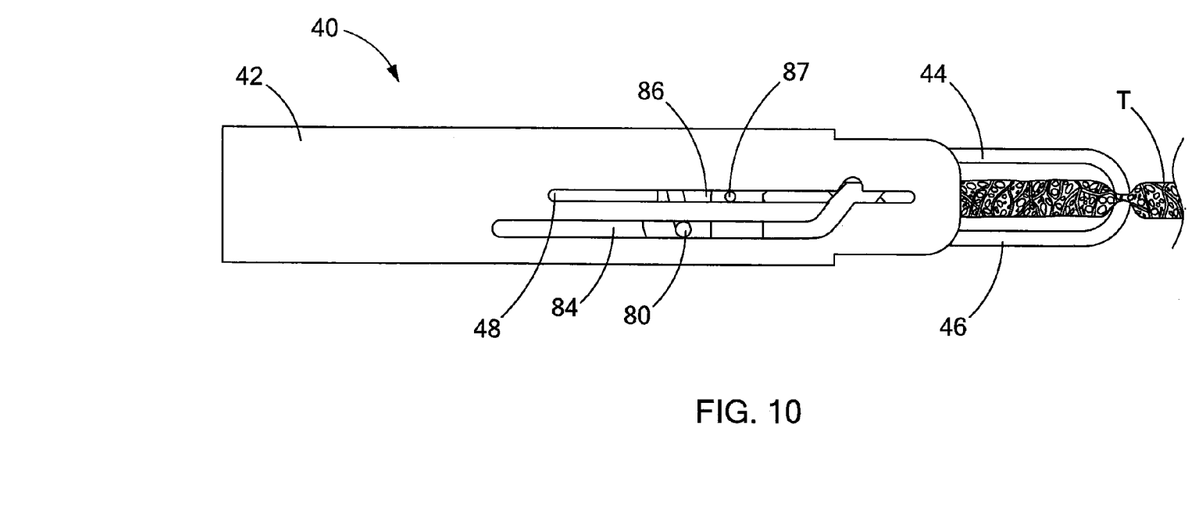

Likewise, the proximal ends of the links 68, 70 and their pins 80 are connect to the flanges 56, 58 of the driver 48 such that proximal retraction of the driver 48 (via drive wire 22) causes the pins 80 to follow the reverse path for closing of the jaws 44, 46, and further retraction causes proximal retraction of the jaws 44, 46 towards the interior space 43 of the housing 42. As shown in FIGS. 9 and 10, once the jaws 44, 46 are positioned in their tissue receiving configuration (open configuration, FIGS. 1 and 2) the medical device 40 and its jaws 44, 46 may be around tissue T and the jaws 44, 46 rotated back towards their closed position. The tissue T has been shown as a single layer, although multiple layers may be clipped between the jaws 44, 46. The tissue T may thus be grasped by the jaws 44, 46, and further proximal retraction of the drive wire 22 and driver 48 will cause the jaws 44, 46 to move longitudinally in a proximal direction (to the left on the page in FIGS. 9-10). Accordingly, it can be seen the medical device provides constant force transmission from the drive wire 22 via the driver 48 and links 68, 70 to the jaws 44, 46 for smooth opening and closing of the jaws due to translation in both he distal and proximal direction.

Figure 11:
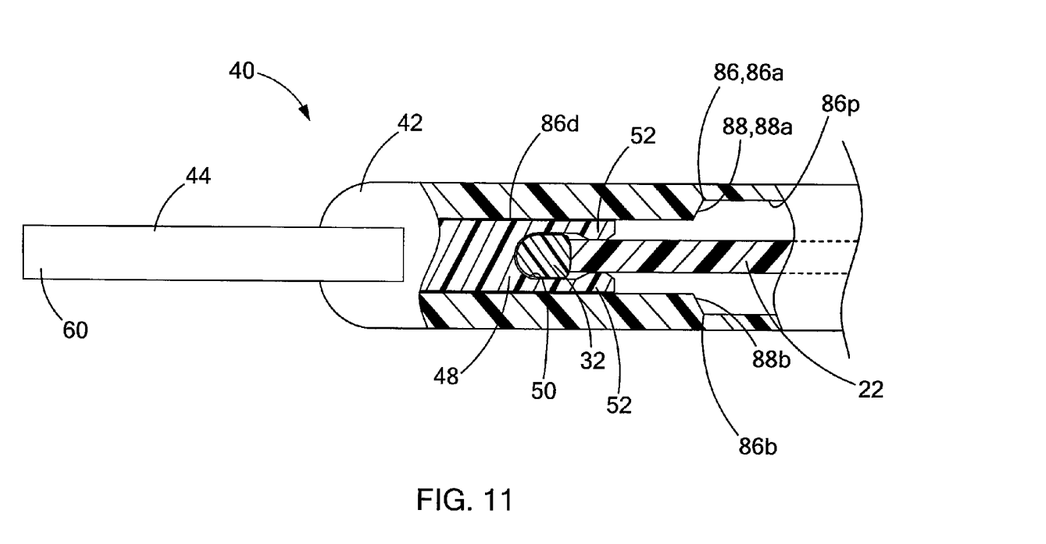
FIGS. 11 and 12 are top views, partially in cross-section, depicting operation of the medical system and device depicted in FIG. 1.

In order for the medical device 40 to serve as a clip and maintain its grasp on the tissue T, or to maintain the clipping of two layers of tissue against each other, the jaws 44, 46 may be locked in position and the drive wire 22 of the medical system 20 disconnected from the medical device 40. As shown in FIG. 11, the interior of the housing 42 also defines a driver guide surface 88 (which guides the driver 48) that has a proximal portion 88p and a distal portion 88d. The proximal portion 88p of the driver guide surface 88 has a width (measured up and down on the page in FIG. 11) that is greater than a width of the distal portion 88d of the driver guide surface 88. The driver guide surface 88 may be formed by opposing surfaces or C-shaped channels in the housing 42. The transition between the proximal portion 88p and distal portion 88d defines a shoulder 89, and namely two shoulders 89a, 89b on opposing sides of the housing 42. The shoulders 89a, 89b are sized and positioned to engage the locking tabs 52, and in particular the sloped portions 54, located on the driver 48.

As shown in FIG. 11, when the driver 48 is located within the distal portion 88d of the driver guide surface 88, the locking tabs 52 are forced radially inwardly into firm frictional engagement with the enlarged head 32 and/or the drive wire 22. Stated another way, the socket 50 formed by the driver 48 that receives the distal head 32 has an entrance which is narrowed by the inward deflection of the locking tabs 52. In this state depicted in FIG. 11, the drive wire 22 is firmly engaged with the driver 48 and hence the first and second jaws 44, 46. When the drive wire 22 and driver 48 are retracted proximally, for example upon grasping tissue as shown in FIGS. 9-10, the proximal end of the driver 48 is received within the proximal portion 88p of the third guide surface 88 which has a larger width that permits outward movement of the locking tabs 52.

Figure 12:
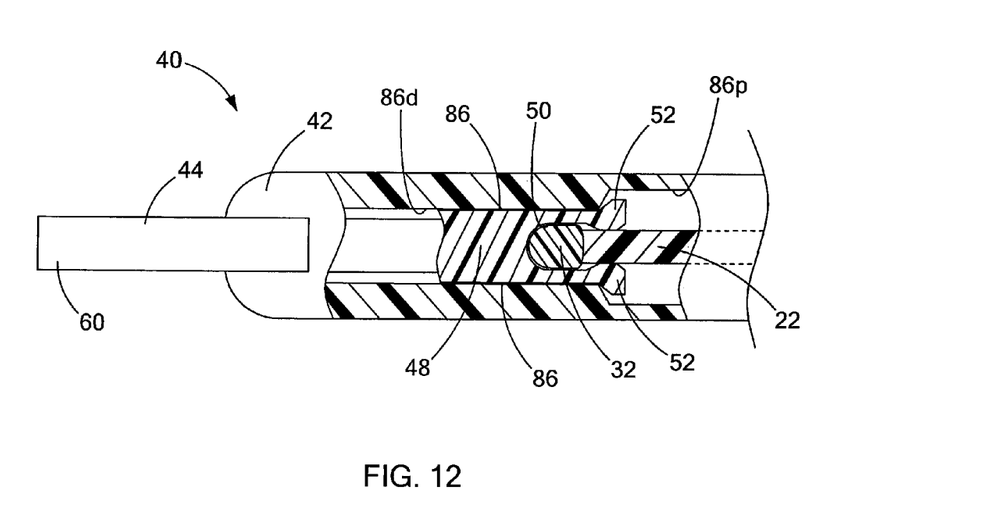

Accordingly, in the state depicted in FIG. 12, the locking tabs 52 may be disconnected from the distal head 32 of the drive wire 22. As such, further proximal movement of the drive wire 22 and its distal head 32 may be used to withdraw the distal head 32 from the socket 50 of the driver 48. At the same time, the locking tabs 52 move radially outwardly and into engagement with the shoulders 89a, 89b to lock the device 40 in a state where the tissue T is clipped between the jaws 44, 46. In the event the natural elasticity of the tissue T tends to pull the jaws 44, 46 out from the housing towards their extended position, the locking tabs 52 will abut the shoulders 89 of the driver guide surface of the housing 42 to prevent further distal movement or rotation of the jaws 44, 46. Preferably, the locking tabs 52 are formed from a material that is plastically deformable, such as a metal or alloy (e.g. Nitinol), such that they plastically deform outwardly to firmly engage the housing 42 and maintain the tissue T between the jaws 44, 46 and the distal end of the housing 42.

Figure 13:
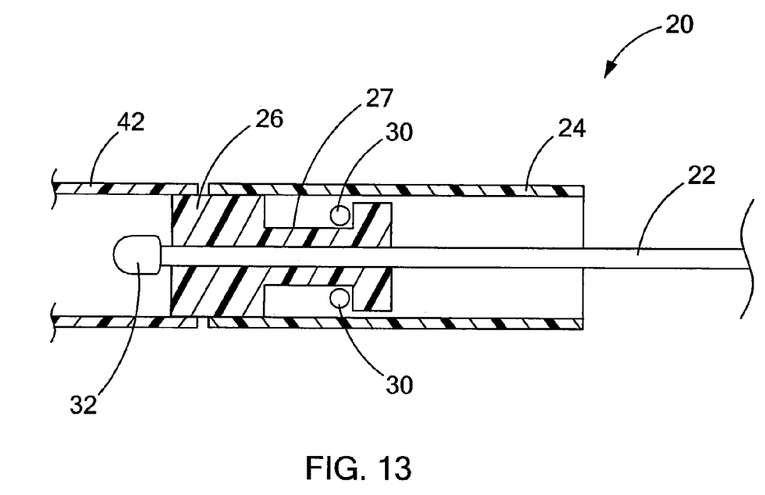
FIGS. 13 and 14 are cross-sectional views showing operation of the medical system depicted in FIG. 1.
Figure 14:
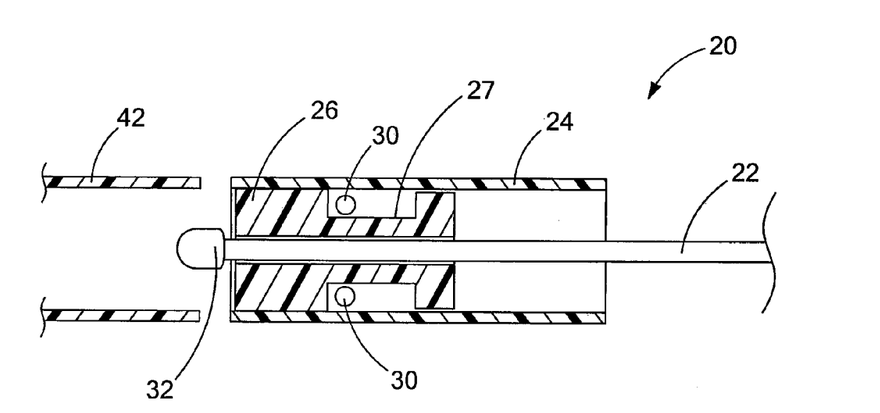

Turning now to FIGS. 13 and 14, upon still further proximal retraction of the drive wire 22 and distal head 32 (to the right on the page), the enlarged distal head 32 (or other enlarged portion of the drive wire 22) will abut the connection block 26, which is slidably fitted within the distal end 23 of the catheter 24. Sufficient proximal force on the drive wire 22 will overcome the frictional fit between the connection block 26 and the proximal end of the housing 42, thus moving the connection block 26 proximally to retract the connection block 26 within the tubular connector 24, as shown in FIG. 14. The catheter 24 can be used to provide a counterforce on the housing 42 while proximally retracting the drive wire 22 and connection block 26. Accordingly, the drive wire 22, catheter 24 and connection block 26 may be fully disconnected from the medical device 40, thereby leaving the first and second jaws 44, 46 and the housing 42 in a state having the tissue T clipped between the jaws 44, 46 and retained in vivo. The connection block 26 is retained at the distal end 24 of the catheter 24 via the pins 30, which are positioned within the recessed area 27 to engage the proximal and distal ends of the connection block 26 and limit its longitudinal movement.

The elongate catheter 24 (or other elongate tubular member such as a sheath, tube, scope or the like), which slidably encases the drive wire 22, extends proximally therealong to a proximal end of the system 20, and has a length suitable for placing the device 40 at any desire location within the body, while the proximal ends of drive wire 22 and catheter 24 are positioned outside of the body for use by the medical professional. Control handles (not shown) for controlling relative translation of the drive wire 22 and catheter 24 are well known in the art, and may be employed at the proximal end of the system 20. Additional embodiments of the connection/disconnection mechanisms and the medical system 20 may be found in copending application U.S. application Ser. Nos. 13/270,834, 13/270,784, 13/270,852, and 12/971,873, filed on Oct. 11, 2011 and Dec. 17, 2010, the disclosures of which are hereby incorporated by reference in its entirety.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical device for engaging tissue, the medical device comprising:
   a housing defining an internal passageway and a longitudinal axis extending between proximal and distal ends of the housing, the housing defining a jaw guide surface, a first link guide surface and a second link guide surface, each of the guide surfaces extending longitudinally between proximal and distal portions of the guide surfaces;
   a first jaw slidably and pivotally connected to the housing, the first jaw having proximal and distal ends, the first jaw slidably received within the internal passageway for longitudinal movement along the jaw guide surface;
   a second jaw slidably and pivotally connected to the housing, the second jaw having proximal and distal ends, the second jaw slidably received within the internal passageway for longitudinal movement along the jaw guide surface;
   a first link having first and second ends, the first end non-rotatably attached to a longitudinal mid-section of the first jaw, the second end slidably and pivotally attached to the housing for longitudinal movement along the first link guide surface;
   a second link having first and second ends, the first end non-rotatably attached to a longitudinal mid-section of the second jaw, the second end slidably and pivotally attached to the housing for longitudinal movement along the second link guide surface; and
   a driver operatively connected to the first and second jaws, longitudinal movement of the driver moving the first and second jaws longitudinally along the jaw guide surface and moving the second ends of the first and second links along the first and second link guide surfaces, and wherein the distal portions of the first and second link guide surfaces are shaped such that longitudinal movement of the second ends of the first and second links therethrough rotates the first and second jaws relative to the housing.

2. The medical device of claim 1, wherein the jaw guide surface is arranged parallel to a jaw plane extending through the longitudinal axis, and wherein the first link guide surface extends along a first link path spaced away from the jaw plane, and the second link guide surface extends along a second link path spaced away from the jaw plane.

3. The medical device of claim 2, wherein the first and second link paths are spaced on opposite sides of the jaw plane.

4. The medical device of claim 1, wherein the first and second links are generally C-shaped and defined by a mid-section interconnecting a proximal-section and a distal-section.

5. The medical device of claim 4, wherein the first jaw is substantially positioned on a first side of the jaw plane, and the second jaw is substantially positioned on a second side of the jaw plane, and wherein the mid-section of the first link is positioned on the second side of the jaw plane, and the mid-section of the second link is positioned on the first side of the jaw plane.

6. The medical device of claim 1, wherein the first and second link guide surfaces each has a proximal portion extending parallel to the longitudinal axis, and a distal portion extending transversely relative to the proximal portion.

7. The medical device of claim 6, wherein the distal portions of the first and second jaw guide surfaces extend towards the jaw plane.

8. The medical device of claim 1, wherein the driver is engaged with the second ends of the first and second links when the driver is moved both distally and proximally.

9. The medical device of claim 8, wherein the driver is engaged with the proximal ends of the first and second jaws when the driver is moved distally.

10. The medical device of claim 1, wherein the proximal ends of the first and second jaws are slidably and pivotally attached to the housing.

11. The medical device of claim 10, wherein the proximal ends of the first and second jaws are pivotally attached to the housing about a shared jaw pivot axis.

12. The medical device of claim 1, wherein the second ends of the first and second links are slidably and pivotally connected to the housing.

13. The medical device of claim 1, wherein the distal portions of the first and second link guide surfaces extend vertically towards each other.

14. The medical device of claim 13, wherein the distal portions of the first and second link guide surface cross over the jaw guide surface.

15. A medical device for engaging tissue, the medical device comprising:
   a housing defining an internal passageway and a longitudinal axis extending between proximal and distal ends of the housing, the housing defining a jaw guide surface, a first link guide surface and a second link guide surface, each of the guide surfaces extending longitudinally between proximal and distal portions of the guide surfaces;
   a first jaw slidably and pivotally connected to the housing, the first jaw having proximal and distal ends, the first jaw slidably received within the internal passageway for longitudinal movement along the jaw guide surface;
   a second jaw slidably and pivotally connected to the housing, the second jaw having proximal and distal ends, the second jaw slidably received within the internal passageway for longitudinal movement along the jaw guide surface;
   a first link having first and second ends, the first end fixedly attached to the first jaw, the second end slidably and pivotally attached to the housing for longitudinal movement along the first link guide surface;
   a second link having first and second ends, the first end fixedly attached to the second jaw, the second end slidably and pivotally attached to the housing for longitudinal movement along the second link guide surface; and
   a driver operatively connected to the first and second jaws, longitudinal movement of the driver moving the first and second jaws longitudinally along the jaw guide surface and moving the second ends of the first and second links along the first and second link guide surfaces, and wherein the distal portions of the first and second link guide surfaces are shaped such that longitudinal movement of the second ends of the first and second links therethrough rotates the first and second jaws relative to the housing, wherein the driver includes a distal end having at least one slot being elongated, the at least one slot pivotally and slidably receiving the second ends of the first and second links.

16. The medical device of claim 15, further comprising a first link pivot pin that pivotally connects the second end of the first link to the housing, and further comprising a second link pivot pin that pivotally connects the second end of the second link to the housing.

17. The medical device of claim 16, wherein the distal end of the driver includes a first flange laterally spaced apart from a second flange, the at least one slot including a first slot formed in the first flange and receiving the first link pin, and a second slot formed in the second flange and receiving the second link pin.

18. The medical device of claim 16, wherein the first link guide surface is defined by a first link slot formed in the housing, and wherein the second link guide surface is defined by a second link slot formed in the housing, and wherein the first link slot is positioned on an opposite side of the housing as the second link slot.

19. The medical device of claim 15, wherein the distal end of the driver includes driver end surface located distal to the at least one slot, the end surface abutting the proximal ends of the jaws.

20. A medical device for engaging tissue, the medical device comprising:
   a housing defining an internal passageway and a longitudinal axis extending between proximal and distal ends of the housing, the housing defining a jaw guide surface, a first link guide surface and a second link guide surface, each of the guide surfaces extending longitudinally between proximal and distal portions of the guide surfaces;
   a first jaw slidably and pivotally connected to the housing, the first jaw having proximal and distal ends, the first jaw slidably received within the internal passageway for longitudinal movement along the jaw guide surface;
   a second jaw slidably and pivotally connected to the housing, the second jaw having proximal and distal ends, the second jaw slidably received within the internal passageway for longitudinal movement along the jaw guide surface;
   a first link having first and second ends, the first end fixedly attached to the first jaw, the second end slidably and pivotally attached to the housing for longitudinal movement along the first link guide surface;
   a second link having first and second ends, the first end fixedly attached to the second jaw, the second end slidably and pivotally attached to the housing for longitudinal movement along the second link guide surface; and
   a driver operatively connected to the first and second jaws, longitudinal movement of the driver moving the first and second jaws longitudinally along the jaw guide surface and moving the second ends of the first and second links along the first and second link guide surfaces, and wherein the distal portions of the first and second link guide surfaces are shaped such that longitudinal movement of the second ends of the first and second links therethrough rotates the first and second jaws relative to the housing, wherein the distal end of the driver includes a driver end surface directly abutting the proximal ends of the jaws.

21. The medical device of claim 20, wherein the first ends of the first and second links are non-rotatably attached to a longitudinal mid-section of the first and second jaws, respectively.

22. The medical device of claim 20, wherein the first jaw is substantially positioned on a first side of the jaw plane, and the second jaw is substantially positioned on a second side of the jaw plane, and wherein the mid-section of the first link is positioned on the second side of the jaw plane, and the mid-section of the second link is positioned on the first side of the jaw plane.

23. The medical device of claim 20, wherein the driver includes a distal end having at least one slot receiving the first and second link pins, the at least one slot being elongated and slidably receiving the first and second link pins.

* * * * *